United States Patent
Kaujalgikar et al.

(10) Patent No.: US 9,593,091 B2
(45) Date of Patent: Mar. 14, 2017

(54) METHODS FOR MAKING EPOXIDIZED FATTY ACID ALKYL ESTERS

(71) Applicant: Dow Global Technologies LLC, Midland, MI (US)

(72) Inventors: Saurabh Kaujalgikar, Pune (IN); Neeta Rao, Pune (IN); Bharat I. Chaudhary, Princeton, NJ (US); Abhijit Ghosh-Dastidar, East Brunswick, NJ (US)

(73) Assignee: Dow Global Technologies LLC, Midland, MI (US)

( * ) Notice: Subject to any disclaimer, the term of this patent is extended or adjusted under 35 U.S.C. 154(b) by 0 days.

(21) Appl. No.: 14/429,093

(22) PCT Filed: Nov. 12, 2012

(86) PCT No.: PCT/IN2012/000745
§ 371 (c)(1),
(2) Date: Mar. 18, 2015

(87) PCT Pub. No.: WO2014/072986
PCT Pub. Date: May 15, 2014

(65) Prior Publication Data
US 2015/0252014 A1 Sep. 10, 2015

(51) Int. Cl.
| | |
|---|---|
| *C07D 301/00* | (2006.01) |
| *C07D 303/42* | (2006.01) |
| *C07D 301/12* | (2006.01) |
| *C08K 5/00* | (2006.01) |
| *C08K 5/1515* | (2006.01) |

(52) U.S. Cl.
CPC ......... *C07D 303/42* (2013.01); *C07D 301/00* (2013.01); *C07D 301/12* (2013.01); *C08K 5/0016* (2013.01); *C08K 5/1515* (2013.01)

(58) Field of Classification Search
CPC .. C08K 5/1515; C08K 5/0016; C07D 301/00; C07D 301/12; C07D 303/42; C08L 27/08
See application file for complete search history.

(56) References Cited

U.S. PATENT DOCUMENTS

| | | |
|---|---|---|
| 2,397,592 A | 4/1946 | Blades |
| 2,403,215 A | 7/1946 | Foster |
| 2,458,484 A | 1/1949 | Terry et al. |
| 2,500,918 A | 3/1950 | Rueter et al. |
| 2,618,622 A | 11/1952 | Grummit et al. |
| 2,666,752 A | 1/1954 | Grummit et al. |
| 3,138,566 A | 6/1964 | Arnold |
| 3,381,837 A | 5/1968 | Testa et al. |
| 3,409,580 A | 11/1968 | Atzner |
| 3,451,958 A | 6/1969 | Riedeman et al. |
| 3,639,318 A | 2/1972 | Tijunelis et al. |
| 3,668,091 A | 6/1972 | French et al. |
| 3,712,875 A | 1/1973 | Tijunelis |
| 3,778,465 A | 12/1973 | Barnstorf |
| 3,780,140 A | 12/1973 | Hammer |
| 3,868,341 A | 2/1975 | Sauer et al. |
| 3,872,187 A | 3/1975 | Fath |
| 3,891,694 A | 6/1975 | Mills et al. |
| 4,083,816 A | 4/1978 | Frankel et al. |
| 4,346,145 A | 8/1982 | Choi et al. |
| 4,421,886 A | 12/1983 | Worschech et al. |
| 4,426,477 A | 1/1984 | Yasumatsu et al. |
| 4,556,694 A | 12/1985 | Wallace |
| 4,605,694 A | 8/1986 | Walker |
| 4,612,192 A | 9/1986 | Scheuffgen et al. |
| 4,613,533 A | 9/1986 | Loomis et al. |
| 4,627,993 A | 12/1986 | Loomis |
| 4,670,494 A | 6/1987 | Semenza, Jr. |
| 4,857,600 A | 8/1989 | Gross et al. |
| 5,225,108 A | 7/1993 | Bae et al. |
| 5,227,417 A | 7/1993 | Kroushl, III |
| 5,246,783 A | 9/1993 | Spenadel et al. |
| 5,270,366 A | 12/1993 | Hein |
| 5,278,236 A | 1/1994 | Case et al. |
| 5,430,108 A | 7/1995 | Schlosberg et al. |
| 5,454,806 A | 10/1995 | Shinonome |
| 5,464,903 A | 11/1995 | Hofmann |
| 5,466,267 A | 11/1995 | Baillargeon et al. |
| 5,575,965 A | 11/1996 | Caronia et al. |
| 5,736,605 A | 4/1998 | Oshima |
| 5,756,570 A | 5/1998 | Hoch et al. |

(Continued)

FOREIGN PATENT DOCUMENTS

| | | |
|---|---|---|
| CA | 1188445 A1 | 6/1985 |
| CN | 1341681 | 3/2002 |

(Continued)

OTHER PUBLICATIONS

PCT/US2011/035143, International Preliminary Report on Patentability, Issued Nov. 10, 2012.
PCT/US2011/041557 International Preliminary Report on Patentability, Mailed Aug. 31, 2012.
PCT/US2011/041557 International Search Report and Written Opinion Mailed Sep. 5, 2011.
PCT/US2011/045653 International Search Report and Written Opinion, Mailed Oct. 7, 2011.
PCT/US2011/045653, International Preliminary Report on Patentability, Issued Jan. 28, 2013.

(Continued)

*Primary Examiner* — Peter D Mulcahy

(57) ABSTRACT

Methods for making epoxidized fatty acid alkyl esters. Such epoxidized fatty acid alkyl esters can be prepared by epoxidizing a natural oil with an acid and a peroxide. Residual acid in the epoxidized natural oil is not neutralized, such as with a base, prior to esterification to produce the epoxidized fatty acid alkyl esters. Epoxidized fatty acid alkyl esters can be employed in plasticizers, either alone or in combination with other plasticizers, such as epoxidized natural oils. Such plasticizers in turn may be used in the formation of polymeric compositions.

18 Claims, No Drawings

(56) References Cited

U.S. PATENT DOCUMENTS

| | | | |
|---|---|---|---|
| 5,886,072 | A | 3/1999 | Linsky et al. |
| 6,063,846 | A | 5/2000 | Weng et al. |
| 6,114,425 | A | 9/2000 | Day et al. |
| 6,274,750 | B1 | 8/2001 | Sato et al. |
| 6,417,260 | B1 | 7/2002 | Weng et al. |
| 6,437,170 | B1 | 8/2002 | Thil et al. |
| 6,451,958 | B1 | 9/2002 | Fan et al. |
| 6,495,033 | B1 | 12/2002 | Talboom |
| 6,496,629 | B2 | 12/2002 | Ma et al. |
| 6,608,142 | B1 | 8/2003 | Weng et al. |
| 6,706,815 | B2 | 3/2004 | Marchand et al. |
| 6,714,707 | B2 | 3/2004 | Rossi et al. |
| 6,734,241 | B1 | 5/2004 | Nielsen et al. |
| 6,797,753 | B2 | 9/2004 | Benecke et al. |
| 6,849,694 | B2 | 2/2005 | Hata |
| 6,949,597 | B2 | 9/2005 | Nielsen et al. |
| 7,700,675 | B2 | 4/2010 | Bueno de Almeida et al. |
| 2002/0013396 | A1 | 1/2002 | Benecke et al. |
| 2004/0122159 | A1 | 6/2004 | Mhetar et al. |
| 2005/0090590 | A1 | 4/2005 | Nielsen et al. |
| 2005/0203230 | A1 | 9/2005 | Kadakia et al. |
| 2006/0025544 | A1 | 2/2006 | Koube et al. |
| 2006/0276575 | A1 | 12/2006 | Hamaguchi et al. |
| 2007/0100049 | A1 | 5/2007 | Ishizuka |
| 2007/0135562 | A1 | 6/2007 | Freese et al. |
| 2008/0200595 | A1 | 8/2008 | Hinault et al. |
| 2008/0227993 | A1 | 9/2008 | Zuckerman |
| 2009/0149585 | A1 | 6/2009 | De Quadros Junior et al. |
| 2009/0149586 | A1 | 6/2009 | De Quadros Junior et al. |
| 2009/0306257 | A1 | 12/2009 | Wehner et al. |
| 2009/0312478 | A1 | 12/2009 | Hasegawa et al. |
| 2010/0010127 | A1 | 1/2010 | Barki et al. |
| 2010/0256278 | A1 | 10/2010 | Harada et al. |
| 2011/0076502 | A1 | 3/2011 | Chaudhary et al. |
| 2011/0272174 | A1 | 11/2011 | Chaudhary |
| 2012/0136169 | A1 | 5/2012 | Abraham et al. |
| 2013/0005937 | A1 | 1/2013 | Cramail et al. |

FOREIGN PATENT DOCUMENTS

| | | |
|---|---|---|
| CN | 101070510 | 11/2007 |
| CN | 101108982 A | 1/2008 |
| CN | 101591588 A | 12/2009 |
| CN | 101824193 A | 9/2010 |
| CN | 101914219 A | 12/2010 |
| EP | 0192961 A1 | 9/1986 |
| EP | 0358179 A2 | 3/1990 |
| EP | 0364717 A1 | 4/1990 |
| EP | 0 393 813 A1 | 10/1990 |
| EP | 0473915 A1 | 3/1992 |
| EP | 0565984 A1 | 10/1993 |
| EP | 0986606 A1 | 3/2000 |
| EP | 1218443 A1 | 7/2002 |
| EP | 1361039 A1 | 11/2003 |
| EP | 1624014 A1 | 2/2006 |
| EP | 2070977 A2 | 6/2009 |
| EP | 2245089 A1 | 11/2010 |
| FR | 1437722 A | 5/1966 |
| GB | 499931 A | 1/1939 |
| GB | 790314 A | 2/1958 |
| GB | 805252 A | 12/1958 |
| GB | 910543 A | 11/1962 |
| GB | 934689 A | 8/1963 |
| GB | 1022920 A | 3/1966 |
| GB | 1102506 A | 2/1968 |
| GB | 1341623 A | 12/1973 |
| GB | 1382853 A | 2/1975 |
| GB | 2155021 A | 9/1985 |
| JP | S44-007131 | 3/1969 |
| JP | S61-016950 | 1/1986 |
| JP | 04-059851 B2 | 2/1992 |
| JP | H04-085354 | 3/1992 |
| JP | H04-261452 A | 9/1992 |
| JP | 2000-319468 A | 11/2000 |
| JP | 2003-064233 A | 3/2003 |
| JP | 2003-297149 A | 10/2003 |
| JP | 2004311064 A | 11/2004 |
| JP | 2010-042669 A | 2/2010 |
| WO | 9730115 A1 | 8/1997 |
| WO | 0114466 A1 | 3/2001 |
| WO | 0198404 A2 | 12/2001 |
| WO | 2004052977 A1 | 6/2004 |
| WO | 2007006489 A1 | 1/2007 |
| WO | 2008081330 A1 | 7/2008 |
| WO | 2008081332 A1 | 7/2008 |
| WO | 2008122364 A1 | 10/2008 |
| WO | 2009102877 A1 | 8/2009 |
| WO | 2011/041380 A1 | 4/2011 |
| WO | 2011/041388 A1 | 4/2011 |
| WO | 2011041372 A1 | 4/2011 |
| WO | 2012130545 A1 | 10/2012 |
| WO | 2013003225 A2 | 1/2013 |

OTHER PUBLICATIONS

PCT/US2011/059166 International Search Report and Written Opinion, Mailed Feb. 29, 2012.
PCT/US2011/059166, International Preliminary Report on Patentability, Issued May 7, 2013.
PCT/US2012/043740 International Search Report and Written Opinion, Mailed Jan. 23, 2013.
PCT/US2012/043740, International Preliminary Report on Patentability, Issued Jan. 7, 2014.
PCT/US2012/055070 International Search Report and Written Opinion, Mailed Dec. 3, 2012.
PCT/US2012/055070, International Preliminary Report on Patentability, Issued Apr. 1, 2014.
PCT/US2013/023362 International Search Report and Written Opinion, Mailed Mar. 28, 2013.
PCT/US2013/023362, International Preliminary Report on Patentability, Issued Aug. 12, 2014.
PCT/US2013/039840 International Search Report and Written Opinion, Mailed Jul. 11, 2013.
PCT/US2013/039840, International Preliminary Report on Patentability, Issued Dec. 31, 2014.
PCT/US2013/039841, International Preliminary Report on Patentability, Issued Dec. 21, 2014.
PCT/US2013/039841, International Search Report and Written Opinion, Mailed Mar. 27, 2014.
PCT/US2014/020556 International Preliminary Report on Patentability, Issued Sep. 24, 2015.
PCT/US2014/020556 International Search Report and Written Opinion, Mailed Jun. 25, 2014.
Alejandrina Campanella et al.; High Yield Epoxidation of Fatty Acid Methyl Esters with Performic Acid Generated In Situ; Chemical Engineering Journal, 144 (2008) 466-475 (Elsevier B.V.).
Barnicoat, C.R. 1945. Reactions and properties of annatto as a cheese colour. Part II. J. Dairy Res. 14: 59-63.
Bizzari, S.N. et al (2003), Plasticizers. CEH Marketing Research Report, 38-64, Retrieved from http://www.sriconsulting.com.
Chuanshang Cai, et al.; Studies on the Kinetics of In Situ Epoxidation of Vegetable Oils; Eur. J. Lipid Sci. Technol., 2008, 110, 341-346 (Wiley-VCH GmbH & Co. KGaA, Weinheim).
Corrigan, Brian Oil purification, filtration and reclamation, Iron Age (1947) 159(14).
Danisco, Grindsted Soft-n-Safe brochure 2007/2008.
Dow Global Technologies LLC, EP Appln No. 12839186.9-1454, Rejection dated Jul. 9, 2015.
Dow Global Technologies LLC, EP Appln No. 12839186.9-1454, Response dated Dec. 30, 2015.
Du G., et al., Catalytic Epoxidation of Methyl Linoleate, JAOCS, vol. 81, No. 4 (2004).
E. Santacesaria et al.; A Biphasic Model Describing Soybean Oil Epoxidation with $H_2O_2$ in a Fed-Batch Reactor; Chemical Engineering Journal, vol. 173, Issue 1, Sep. 1, 2011, pp. 198-209 (Elsevier B.V.).
Erythropel H. C. et al; "Designing green plasticizers: Influence of molecular geometry on biodegradation and plasticization properties", Chemosphere, Pergamon Press, Oxford, GB, vol. 86, No. 8, Nov. 21, 2011, pp. 759-766.

(56) References Cited

OTHER PUBLICATIONS

Freedman, F., Butterfield, R., and Pryde, E.H. Transesterification Kinetics of Soybean Oil. JAOCS, 63(10) p. 1375 (1986).
Gan, L. H., et al (1994) Epozidized esters of palm olein as plasticizers for poly (vinyl chloride). European Polymer Journal, 31(8), 719-724.
Greenspan, F. P. et al (1953) Epoxy fatty acid ester plasticizers. Indstrial and Engineering Chemistry, 445(12), 2722-2726.
Greenspan, F.P. et al (1956), Epoxy fatty acid ester plasticizers. Preparartion and properties, The Journal of the American Oil Chemists Society, 33, 391-394.
Grummitt O. and Fleming H. Acetylated Castor Oil Industrial and Engineering Chemistry, vol. 37, No. 5, May 1945, pp. 485-491.
Haas, Michael J. Improving the Economics of biodiesel production through the use of low value lipids as feedstocks: vegetable oil soapstock, Fuel Processing Technology 86 p. 1087-96 (2005).
Jensen, R.G. Purification of Triglycerides with an Aluminca Column, Lipids, 451-452 (1966).
Kastner J. et al; Aqueous leaching of di-2-ethylhexyl phthalate and green plasticizers from poly(vinyl chloride) , Science of the Total Enviomment, Elsevier, Amsterdam, NL, vol. 432, Jun. 5, 2012, pp. 357-364.
Morgenstern, B. "Epoxidized Fatty Acid Esters as Plasticizers for PVC" dated Apr. 22, 2005.
Morgenstern, B. Epoxidized Fatty Acid Esters as Plasticizers for PVC, presented at the 7th Freiberg Polymer Conference, Apr. 21 and 22, 2005.
Morgenstern, B. Use of Modified Fatty Acid Esters as Plasticizers for PVC, dated Sep. 12, 2003.
Opposition to patent EP2245089, Dated Jan. 9, 2013.
Orellana-Coca et al., Lipase Mediated Simultaneious Esterification and Epoxidation of Oleic Acid for the Production of Alkylepoxystearates. Journal of Molecular Catalysis B: Enzymatic 44 (2007) 133-137.
Rehberg, C. et al. Plasticizers from Lactic Esters and Biabasic Acids Ind. Eng. Chem., 1952, 44 (9), pp. 2191-2195.
Senžana Sinadinovi?-Fišer et al.; Kinetics of In Situ Epoxidation of Soybean Oil in Bulk Catalyzed by Ion Exchange Resin; Journal of the American Oil Chemists' Society, vol. 78, No. 7 (2001) 725-731 (AOCS Press).
Sheehan, J et al. "A Look Back at the U.S. Department of Energy's Aquatic Species Program: Biodiesel from Algae", National Renewable Energy Laboratory, Colorado, Jul. 1998, pp. 1-294.
Stuart, A et al., Polym. Bull. (2010) 65:589-598.
Taylor, D. R. Proceedings of the World Conference on oilseed technology and utilization, Adsorptive Purification, American Oil Chemists Society, Champaing, 1992, p. 152-165.
Tekin A., and Hammond E. Factors Affecting the Electrical Resistivity of Soybean Oil, JAOCS, vol. 75(6) 1998.
XP002657062 Vertellus Performance Materials Inc.; Flexricin P-8 Technical Data Sheet, Nov. 2006.
XP002669860, Thomson Scientific, Mar. 13, 2009, London, GB.
XP002696108, Tables 2-6, Jun. 10, 2006; Retrieved from the Internet. URL: www.fao.org/es/esn/food/bio-10t.pdf.
PCT/ IN2012/000745, International Preliminary Report on Patentability mailed May 21, 2015.
PCT/IN2012/000745 International Search Report and Written Opinion mailed Aug. 29, 2013. PCT/US2009/033935.
International Preliminary Report on Patentability, Mailed Aug. 26, 2010.
PCT/US2009/033935 International Search Report and Written Opinion, Mailed Mailed May 18, 2009.
PCT/IN2012/000746 International Search Report and Written Opinion, Mailed May 31, 2013.
PCT/IN2012/000746, International Preliminary Report on Patentability, Issued May 12, 2015.
PCT/IN2012/00688, International Preliminary Report on Patentability, Issued Apr. 30, 2015.
PCT/IN2012/00688, International Search Report and Written Opinion, Mailed Jun. 18, 2013.
PCT/US2010/050654 International Search Report and Written Opinion Mailed Nov. 9, 2010.
PCT/US2010/050654, International Preliminary Report on Patentability, Issued Mar. 31, 2012.
PCT/US2010/050669, International Preliminary Report on Patentability, Issued Apr. 11, 2012.
PCT/US2010/050699 International Search Report and Written Opinion, Mailed Nov. 8, 2010.
PCT/US2010/050676 International Search Report and Written Opinion Mailed Jan. 12, 2011.
PCT/US2010/050676, International Preliminary Report on Patentability, Issued Mar. 31, 2012.
PCT/US2010/050690 International Preliminary Report on Patentability, Mailed Jan. 12, 2012.
PCT/US2010/050690 International Search Report and Written Opinion, Mailed Aug. 2, 2011.
PCT/US2011/035143 International Search Report and Written Opinion, Mailed Aug. 26, 2011.

METHODS FOR MAKING EPOXIDIZED FATTY ACID ALKYL ESTERS

FIELD

Various embodiments of the present invention relate to methods for making epoxidized fatty acid alkyl esters. Such epoxidized fatty acid alkyl esters may be employed as plasticizers or in plasticizer compositions.

INTRODUCTION

Plasticizers are compounds or mixtures of compounds that are added to polymer resins that can lower the modulus and tensile strength, and increase flexibility, elongation, impact strength, and tear strength of the resin (typically a thermoplastic polymer) to which they are added. A plasticizer may also lower the melting point of the polymer resin, which lowers the glass transition temperature and enhances processability of the polymer resin.

Phthalic acid diesters (also known as "phthalates") are commonly used as plasticizers in many flexible polymer products, such as polymer products formed from polyvinyl chloride ("PVC") and other vinyl polymers. Examples of phthalate plasticizers include diisononyl phthalate, diallyl phthalate, di-2-ethylhexyl-phthalate, dioctyl phthalate, and diisodecyl phthalate. Other plasticizers used for high temperature applications are trimellitates and adipic polyesters.

Phthalate plasticizers have recently come under intense scrutiny by public interest groups concerned about the negative environmental impact of phthalates and potential adverse health effects in humans (especially children) exposed to phthalates.

An epoxidized alkyl ester of soybean oil (e.g., epoxidized fatty acid alkyl ester, or "eFAAE") can be used as a plasticizer for polyvinyl chloride ("PVC") and other polymers (natural rubber, acrylate, etc.) or alternately, it can be used as a primary or secondary plasticizer in a plasticizer blend (such as with epoxidized soybean oil ("eSO")). Although advancements have been made, improvements in such plasticizers are still desired.

SUMMARY

One embodiment is a process for producing epoxidized fatty acid alkyl esters, said process comprising, consisting essentially of, or consisting of:
 (a) epoxidizing a natural oil by contacting said natural oil with an acid and a peroxide to thereby produce an epoxidized reaction mixture comprising epoxidized natural oil, residual acid, residual peroxide, and water;
 (b) removing at least a portion of said residual acid, at least a portion of said residual peroxide, and at least a portion of said water from said epoxidized reaction mixture to thereby produce an intermediate reaction mixture; and
 (c) esterifying at least a portion of said epoxidized natural oil in said intermediate reaction mixture, thereby forming said epoxidized fatty acid alkyl esters,
 wherein said residual acid is not neutralized prior to said esterifying of step (c).

DETAILED DESCRIPTION

Various embodiments of the present invention concern methods for preparing eFAAE from natural oils. Such eFAAEs can be employed as a plasticizer alone or in combination with an epoxidized natural oil ("eNO"). Plasticizers comprising eFAAE and optionally eNO can be employed with a variety of polymeric resins and in making various articles of manufacture.

Preparing Epoxidized Fatty Acid Alkyl Esters

The eFAAE can be prepared by first epoxidizing a natural oil. A "natural oil," as used herein, is an oil comprising fatty acid triglycerides and derived from a microbe (algae, bacteria), a plant/vegetable, and/or a seed. In an embodiment, natural oil includes genetically-modified natural oil. In another embodiment, the natural oil excludes petroleum-derived oil. Non-limiting examples of suitable natural oils include algae oil, beef tallow oil, canola oil, castor oil, corn oil, fish oil, linseed oil, palm oil, rapeseed oil, safflower oil, soybean oil, sunflower oil, tall oil, tung oil, and any combination thereof.

In an embodiment, the natural oil is soybean oil.

The term "epoxidized natural oil," as used herein, is a natural oil wherein at least one fatty acid moiety contains at least one epoxide group. Non-limiting examples of suitable eNO include epoxidized algae oil, epoxidized beef tallow oil, epoxidized canola oil, epoxidized castor oil, epoxidized corn oil, epoxidized fish oil, epoxidized linseed oil, epoxidized palm oil, epoxidized rapeseed oil, epoxidized safflower oil, epoxidized soybean oil, epoxidized sunflower oil, epoxidized tall oil, epoxidized tung oil, and any combination thereof.

In an embodiment, the epoxidized natural oil is an epoxidized soybean oil ("eSO").

In various embodiments, the natural oil is epoxidized by contacting it with an acid and a peroxide to thereby produce an epoxidized reaction mixture comprising an eNO, residual acid, residual peroxide, and water. Thereafter, a portion or at least a portion of the residual acid, residual peroxide, and water is removed from the epoxidized reaction mixture prior to esterifying the eNO to produce the eFAAE, as discussed below.

Suitable acids for use in epoxidizing the natural oil include carboxylic acids, such as formic acid and acetic acid; and peroxycarboxylic acids, such as performic acid and peracetic acid. Catalysts such as mineral acids (e.g., sulfuric acid) and heterogeneous acid resins (e.g., Amberlite™ IR 120H, available from Rohm & Haas) may optionally be employed in the presence of the acid. In an embodiment, the acid employed for epoxidation is formic acid. In an embodiment, the formic acid is employed in the absence of any catalyst.

Suitable peroxides for use in epoxidizing the natural oil include aqueous solutions of hydrogen peroxide, peroxycarboxylic acids, alkyl hydroperoxides, and tertiary hydroperoxides. In an embodiment, the peroxide employed is an aqueous solution of hydrogen peroxide. In various embodiments, the aqueous solution can be a 30 to 50 volume percent ("vol %") solution.

Techniques suitable for removing residual acid, peroxide, and water can comprise layer separation. Layer separation involves separation of an aqueous layer, which contains water, acids, peroxide, and possible traces of oil and esters, from an organic layer containing eNO and eFAME. Following epoxidation, the reaction mixture is allowed to settle and separate into two layers by density difference, and the bottom aqueous layer is disposed of while the top organic layer is processed further to obtain the desired product, as described below.

Removal of residual acid, peroxide, and water can also include vacuum distillation of the epoxidized reaction mixture. In an embodiment, vacuum distillation can be performed on all or some of the organic layer resulting from the above-described layer separation process. Vacuum distillation can be performed employing any known or hereafter discovered distillation techniques and equipment. In this distillation process, the peroxide, acid, and water are removed as the distillate, while eNO is recovered as the bottom fraction. In an embodiment, vacuum distillation can be performed at a temperature ranging from 40 to 80 degrees Celsius ("° C."), from 50 to 70° C., or at 60° C. Additionally, vacuum distillation can be performed under a reduced pressure ranging from 1 to 50 millibar ("mbar") (100 to 5,000 pascals ("Pa")), from 2 to 40 mbar (200 to 4,000 Pa), from 5 to 20 mbar (500 to 2,000 Pa), or at 10 mbar (1,000 Pa). Distillation can be performed for a time ranging from 1 to 5 hours, or from 2 to 3 hours. Additionally, single stage or multi stage distillation may be employed.

Following distillation, the resulting distilled epoxidized reaction mixture can have a water content of less than 0.4 weight percent ("wt %"), less than 0.35 wt %, less than 0.3 wt %, or less than 0.25 wt %, based on the entire weight of the distilled epoxidized reaction mixture.

Following distillation, the resulting distilled epoxidized reaction mixture can have an acid value of less than 1, less than 0.98, less than 0.95, or less than 0.9 milligrams of potassium hydroxide per gram of distilled epoxidized reaction mixture ("mg KOH/g"). Acid value is determined by titration-based techniques as described in ASTM D664. In a typical procedure, a known amount of sample is dissolved in organic solvent (e.g., isopropanol) and is titrated with a solution of potassium hydroxide with known concentration along with phenolphthalein as a color indicator.

In an embodiment, removal of residual acid from the epoxidized reaction mixture does not include neutralization of the residual acid. The terms "neutralization" and "neutralized" denote a chemical reaction between an acid and a base to form a salt. Accordingly, in the instant case, removal of residual acid from the epoxidized reaction mixture does not include reacting the residual acid with a base. In other words, in various embodiments, no base is added to the epoxidized reaction mixture.

In an embodiment, removal of residual acid from the epoxidized reaction mixture does not include water washing the reaction mixture or any portion thereof (e.g., an organic layer formed by layer separation, as described above).

In an embodiment, removal of residual acid from the epoxidized reaction mixture does not include azeotropic distillation.

Following removal of a portion or at least a portion of the residual acid, residual peroxide, and water, the epoxidized natural oil can be transesterified by contact with an alcohol. Alcohols suitable for use in transesterification include $C_1$ to $C_8$ monohydric linear alcohols, such as methanol, ethanol, propanol, and butanol, or $C_3$ to $C_8$ branched alcohols, such as isopropanol, isobutanol, and 2-ethylhexanol. In an embodiment, the alcohol employed for transesterification is methanol. A catalyst may also be employed for transesterification. Catalysts suitable for use in transesterification include homogeneous alkali catalysts, including metal alkoxides such as sodium methoxide, potassium methoxide, and sodium ethoxide, or metal hydroxides such as potassium hydroxide ("KOH"), sodium hydroxide ("NaOH"), or supported solid alkali catalysts. Other classes of catalysts that may also be employed include acids, acidic resins, double metal cyanide ("DMC") catalysts, enzymes, super acids, super bases, metal salts. The catalyst can be in homogeneous or heterogeneous form. In an embodiment, the catalyst employed for transesterification is sodium methoxide solution in methanol.

Depending on the alcohol employed for transesterification, the alkyl moiety of the resulting eFAAE ester may be, for example, a methyl group, an ethyl group, a propyl group, or a 2-ethylhexyl group. As used herein, an "epoxidized fatty acid alkyl ester" is a $C_4$-$C_{24}$ (saturated or unsaturated) carboxylic acid alkyl ester with at least one epoxide group. An "epoxide group" is a three-member cyclic ether (also called oxirane or an alkylene oxide) in which an oxygen atom is joined to each of two carbon atoms that are already bonded to each other. In an embodiment, the eFAAE is an epoxidized fatty acid methyl ester ("eFAME").

In various embodiments, the eFAAE has an American Public Health Association ("APHA") color index value of less than 100, less than 90, less than 80, less than 70, less than 60, or less than 55. APHA color is determined according to ASTM standards E1209 and E313.

Plasticizer

The present disclosure provides a plasticizer comprising an eFAAE, prepared as described above, and optionally an eNO. In an embodiment, the present plasticizer is a phthalate-free plasticizer, or is otherwise void or substantially void of phthalate.

When both eNO and eFAAE are present, the plasticizer can contain relative amounts of eNO (e.g., eSO) to eFAAE (e.g., eFAME) in a weight ratio in the range of from greater than (">") 0:less than ("<") 100 to <100:>0, more typically from 10:90 to 90:10, more typically from 20:80 to 80:20, and even more typically from 30:70 to 70:30. Weight ratios are based on total weight of the plasticizer.

Polymeric Composition

The present disclosure provides a polymeric composition. In an embodiment, a polymeric composition is provided which includes a polymeric resin and the present plasticizer as disclosed above.

Non-limiting examples of suitable polymeric resins include polysulfides, polyurethanes, acrylics, epichlorohydrins, nitrile rubber, chlorosulfonated polyethylene, chlorinated polyethylene, polychloroprene, styrene butadiene rubber, natural rubber, synthetic rubber, EPDM rubber, propylene-based polymers, ethylene-based polymers, and vinyl chloride resins. The term, "propylene-based polymer," as used herein, is a polymer that comprises a majority weight percent polymerized propylene monomer (based on the total amount of polymerizable monomers), and optionally may comprise at least one polymerized comonomer. The term, "ethylene-based polymer," as used herein, is a polymer that comprises a majority weight percent polymerized ethylene monomer (based on the total weight of polymerizable monomers), and optionally may comprise at least one polymerized comonomer.

The term "vinyl chloride resin," as used herein, is a vinyl chloride polymer, such as polyvinyl chloride ("PVC"), or a vinyl chloride copolymer such as vinyl chloride/vinyl acetate copolymer, vinyl chloride/vinylidene chloride copolymer, vinyl chloride/ethylene copolymer or a copolymer prepared by grafting vinyl chloride onto ethylene/vinyl acetate copolymer. The vinyl chloride resin can also include a polymer blend of the above-mentioned vinyl chloride polymer or vinyl chloride copolymer with other miscible or compatible polymers including, but not limited to, chlorinated polyethylene, thermoplastic polyurethane, olefin polymers such as a methacryl polymer or acrylonitrile-butadiene-styrene polymer.

In an embodiment, the polymeric resin is PVC.

In an embodiment, the polymeric composition includes from 25 wt % to 90 wt % PVC, from 5 wt % to 20 wt % eFAAE, from 5 wt % to 20 wt % eNO, and from 0 wt % to 35 wt % filler.

Additives

The polymeric composition may include one or more of the following optional additives: a filler, a flame retardant, a heat stabilizer, an anti-drip agent, a colorant, a lubricant, a low molecular weight polyethylene, a hindered amine light stabilizer, a UV light absorber, a curing agent, a booster, a retardant, a processing aid, a coupling agent, an antistatic agent, a nucleating agent, a slip agent, a viscosity control agent, a tackifier, an anti-blocking agent, a surfactant, an extender oil, an acid scavenger, a metal deactivator, and any combination thereof.

In an embodiment, the polymeric composition includes PVC, the present plasticizer, a filler (calcium carbonate, clays, silica, and any combination thereof), metal soap stabilizers (zinc stearate or mixed metal stabilizers containing Ca, Zn, Mg, Sn, and any combination thereof), a phenolic or related antioxidant, and a processing aid.

Coated Conductor

In an embodiment, the above-described polymeric composition can be employed in forming a coating on a conductor. A "conductor," as used herein, is one or more wire(s) or fiber(s) for conducting heat, light, and/or electricity. The conductor may be a single-wire/fiber or a multi-wire/fiber and may be in strand form or in tubular form. Non-limiting examples of conductors include metals such as silver, gold, copper, carbon, and aluminum. The conductor may also be optical fiber made from either glass or plastic. The coated conductor may be flexible, semi-rigid, or rigid. The coating (also referred to as a "jacket," "sheath," or "insulation") can be on the conductor or on another polymeric layer around the conductor.

TEST METHODS

APHA Color Measurement

Measure liquid color according to ASTM standards E1209 and E313 using a BYK Gardner LCS III™ instrument and measure in APHA units. Set up the bench-top instrument and perform calibration check to insure the instrument is working within specifications. Measure sample color using the protocol listed below:
Set LCS III to measure Hazen/Alpha indices;
Measure each sample via syringe (10 mL) into individual calibrated cuvettes;
Place each loaded cuvette into the LCS III and press the test button; a Hazen/Alpha number is generated. Record this number, remove the sample and place back into the LCS III to measure a second time (record data). Repeat for a third time (record data).
Remove the loaded cuvette and set aside; reset the LCS III to measure Yellowness Index, measure the same cuvette for Yellowness Index (record three measurements).

EXAMPLES

Comparative Example 1

Neutralization, Washing, and Vacuum Drying

Charge 100 g of soybean oil (GEMINI™, available from Cargill) to a reactor along with 13.2 g of formic acid (90% purity, available from S. D. Fine Chemicals). The reaction vessel is a 500-ml three-neck round-bottom flask with variable speed overhead stirrer having a suitable Teflon blade. Immerse the reactor in an oil bath having temperature control for heating/cooling the reactor. The reactor further includes a reflux condenser and a feeding pump for controlled addition of one or more reactants. The reaction can be carried out in batch or semi-batch mode. Preheat the reaction mass to 27-30° C., by maintaining the oil bath temperature at 30° C. Ensure proper mixing in the reactor by mixing the reaction mixture with an overhead stirrer operated at 400 rpm. Add 82.5 g of 50 wt % hydrogen peroxide ("$H_2O_2$" 48-52 wt % aqueous solution, available from MERCK) to the reactor at a flow rate of 50 ml/hr with a peristaltic pump. The pump can be operated at constant speed/variable speed to control the reaction exotherm. Maintain temperature of the reaction mixture below 60° C. during addition by controlling the addition rate of the $H_2O_2$. Once addition of the $H_2O_2$ is complete, heat the reaction mass to 60° C. and allow the reaction to proceed for five hours. At the end of the reaction, subject the reaction mass to layer separation for two hours. During layer separation, the product eNO and unreacted NO are allowed to separate in the form of an upper organic layer while acids, water, and unreacted peroxide separate as a lower aqueous layer. Drain the resulting aqueous layer to separate most of the water and formic acid. Neutralize the organic layer using dilute bicarbonate solution to remove residual formic acid. Prepare a saturated sodium bicarbonate solution by dissolving sodium bicarbonate powder (99% pure, available from Sigma Aldrich) in distilled water which is further diluted in 5 volumes of distilled water to prepare dilute alkali solution for neutralization. 50 mL of this dilute bicarbonate solution is used for neutralization. Thereafter, wash the organic layer with water several times until it becomes neutral. To determine neutrality, the pH of the wash water is measured after each washing using litmus paper and washing is continued until it reaches ~7. A total 150 mL of wash water is required in five washing steps. For each washing step, 30 mL of distilled water is added in the separating funnel containing the organic layer. The mixture is shaken to ensure adequate contact and allowed to settle. Once clear separation is achieved, the bottom aqueous layer is drained and the top organic layer is washed further. The resulting product contains 0.93 wt % water and has an acid value of 0.85 mg KOH/g. Acid value is determined by titrating the product against 0.1 N KOH in presence of solvent using phenolphthalein as color indicator (ASTM D974). Water content is determined by standard Karl Fischer Titration based method (ASTM D789). Remove residual water under vacuum at ~10 mbar (1,000 Pascals ("Pa")) and 60° C. for two hours, reducing the water content to 0.31%, while the acid value remains nearly the same (0.82).

Transesterify this epoxidized product using methanol with sodium methoxide as a catalyst. Mix 44.2 g of epoxidized product with 15 g of methanol (>99% pure, available from Sigma Aldrich) and 1.78 g of 25% sodium methoxide solution in methanol (commercial catalyst solution available from Sigma Aldrich). Perform the reaction at 50° C. for two hours. Wash the end product with water after separating glycerol layer from the bottom. Five water washes with 30 mL each are employed to remove the residual catalyst. Wash water is added in the separating funnel containing crude product and shaken. The mixture is allowed to settle into two distinct layers. The bottom aqueous wash water layer is drained while the top organic layer containing eFAME is subjected to further washing steps. Remove traces of water and methanol under vacuum (~10 mbar (1,000 Pa) vacuum at 60° C.) to obtain the purified product eFAME. The final product properties are provided in Table 1, below.

Comparative Example 2

Azeotropic Distillation

Epoxidize 100 g of soybean oil using the protocol described in Comparative Example 1 up to and including the initial layer separation step. Subject the organic layer containing residual formic acid and water to azeotropic distillation. Water forms an azeotrope with methyl ethyl ketone ("MEK") at 73.5° C. with 89% MEK by weight. Perform azeotropic distillation by adding excess (50 g) MEK (>99% purity, available from Sigma Aldrich) and then distilling off the water-MEK azeotrope at 75 to 80° C. with ambient pressure. Analyze product after azeotropic distillation for moisture content and acid value as described above in Comparative Example 1 and compare with the water content and acid value before azeotropic distillation to determine extent of removal. Water content is reduced from 1.82% to 0.4%, while acid value is reduced from 10.32 to 3.6 after azeotropic distillation. This indicates that water removal is 78.01%, while acid removal is 65.12%.

Transesterify 44.2 g of this mixture using methanol with sodium methoxide as a catalyst as described in Comparative Example 1. Additional 0.5% catalyst is required for this reaction because of high acid value, and excessive foaming is observed during reaction. The final product properties are provided in Table 1, below.

Example 1

Vacuum Distillation (100 g)

Epoxidize 100 g of soybean oil using the protocol described in Comparative Example 1 up to and including the layer separation step. Thereafter, subject the organic layer directly to vacuum distillation to remove residual formic acid and water from the reaction mixture. Perform vacuum distillation at 60° C. and 10 mbar (1,000 Pa) vacuum for two hours. Analyze bottom product after vacuum distillation for moisture content and acid value, and compare with the moisture content and acid value before distillation to determine extent of removal. Moisture content is reduced from 1.77% to 0.24%, while acid value is reduced from 9.51 to 0.88 after vacuum distillation. This indicates that water removal is 87.2% while acid removal was 91.14%. Transesterify 44.2 g of this mixture as described in Comparative Example 1. The final product properties are provided in Table 1, below.

Example 2

Vacuum Distillation (200 g)

Epoxidize 200 g of soybean oil in the same manner as described in Example 1 using 26.4 g of formic acid and 165 g of 50% $H_2O_2$. Maintain addition time, temperature, and reaction time as described in Example 1. Subject the product at the end of epoxidation to vacuum distillation as described in Example 1 for three hours, and analyze for water content and acid value. Water content is reduced from 1.89% to 0.22%, while acid value is reduced from 11.3 to 0.9 after vacuum distillation. This indicates that water removal is 88.86%, while acid removal is 92.38%. Transesterify 44.2 g of this mixture as described in Comparative Example 1. The final product properties are noted in Table 1, below.

TABLE 1

Final eFAME Properties

|  | Comparative Example 1 | Comparative Example 2 | Example 1 | Example 2 |
|---|---|---|---|---|
| Oxirane oxygen | 7.11 | 7.08 | 7.12 | 7.06 |
| Iodine value | 1.3 | 1.1 | 1.2 | 1.32 |
| % Yield (eFAME) | 92.2% | 85.28% | 95.2% | 94.48% |
| % moisture | 0.33% | 0.4% | 0.24% | 0.22% |
| Acid value | 0.51 | 0.92 | 0.46 | 0.48 |

Example 3

Comparison of Vacuum Distillation with Conventional/Other Processes

Epoxidized soybean oil ("eSO") samples (prior to esterification) from Examples 1 and 2 are compared to those obtained in Comparative Examples 1 and 2. Key product specifications, such as percent oxirane oxygen and iodine value, are measured to assess the product quality. Oxirane oxygen content is determined according to ASTM D1652. Iodine value is determined according to ASTM D5768. In addition, water content and acid value are obtained to compare the extent of separation achieved by vacuum distillation process as well as for the conventional/other processes. A summary of these product analyses is noted in Table 2, below.

TABLE 2 eSO Properties (comparison of various downstream processes)

|  | Oxirane oxygen (%) | Iodine value | Moisture content (%) | Acid value |
|---|---|---|---|---|
| Target Final Product Specification for eSO | >6.5 | <5 | <0.4% | <1 |
| Comparative Example 1: eSO after neutralization & washing + vacuum drying | 7.11 | 1.3 | 0.31 | 0.82 |
| Comparative Example 2: eSO after azeotropic distillation | 7.08 | 1.1 | 0.4 | 3.6 |
| Example 1: eSO after vacuum distillation (100 g scale) | 7.12 | 1.2 | 0.24 | 0.88 |
| Example 2: eSO after vacuum distillation (200 g scale) | 7.06 | 1.32 | 0.22 | 0.9 |

Example 4

Color Analysis and Comparison

Analyze each of the samples described above in Comparative Examples 1 and 2, and Examples 1 and 2, for color both at the ESO stage (i.e., prior to transesterification) and following transesterification. Color analyses are performed according to the test method described above. The results of the color analyses for the ESO stage samples are provided in Table 3, below; results from the color analyses for the transesterified samples are provided in Table 4, below.

TABLE 3 eSO Color Properties

| | Color Value (APHA) |
|---|---|
| Target Final Product Specification | 175 max |
| Comparative Example 1 Neutralization & washing + vacuum drying | 130 |
| Comparative Example 2 Azeotropic distillation | 126 |
| Example 1 Vacuum distillation (100 g scale) | 128 |
| Example 2 Vacuum distillation (200 g scale) | 131 |

TABLE 4 eFAME Color Properties

| | Color Value (APHA) |
|---|---|
| Target Final Product Specification | 175 max |
| Comparative Example 1: Neutralization & washing + vacuum drying + transesterification | 154 |
| Comparative Example 2: Azeotropic distillation + transesterification | 132 |
| Example 1: Vacuum distillation + transesterification (100 g scale) | 40 |
| Example 2: Vacuum distillation + transesterification (200 g scale) | 51 |

Although no color value improvement was noted in the eSO samples, the final eFAME samples of Examples 1 and 2 exhibited substantially decreased color values compared to Comparative Examples 1 and 2.

The invention claimed is:

1. A process for producing epoxidized fatty acid alkyl esters, said process comprising:
   (a) epoxidizing a natural oil by contacting said natural oil with an acid and a peroxide to thereby produce an epoxidized reaction mixture comprising epoxidized natural oil, residual acid, residual peroxide, and water;
   (b) removing a portion of said residual acid, at least a portion of said residual peroxide, and at least a portion of said water from said epoxidized reaction mixture to thereby produce an intermediate reaction mixture; and
   (c) esterifying at least a portion of said epoxidized natural oil in said intermediate reaction mixture, thereby forming said epoxidized fatty acid alkyl esters,
   wherein said residual acid is not neutralized prior to said esterifying of step (c).

2. A process for producing epoxidized fatty acid alkyl esters, said process consisting essentially of:
   (a) epoxidizing a natural oil by contacting said natural oil with an acid and a peroxide to thereby produce an epoxidized reaction mixture comprising epoxidized natural oil, residual acid, residual peroxide, and water;
   (b) removing a portion of said residual acid, at least a portion of said residual peroxide, and at least a portion of said water from said epoxidized reaction mixture to thereby produce an intermediate reaction mixture; and
   (c) esterifying at least a portion of said epoxidized natural oil in said intermediate reaction mixture, thereby forming said epoxidized fatty acid alkyl esters.

3. The process of claim 1, wherein said removing of step (b) comprises subjecting said epoxidized reaction mixture to layer separation, thereby forming an organic phase and an aqueous phase, and further comprising subjecting at least a portion of said organic phase to vacuum distillation, thereby forming said intermediate reaction mixture.

4. The process of claim 1, wherein said intermediate reaction mixture has an acid value of less than 1 mg KOH/g.

5. The process of claim 1, wherein said epoxidized fatty acid alkyl esters have an APHA color value of less than 100.

6. The process of claim 1, wherein said peroxide comprises hydrogen peroxide, wherein said acid comprises formic acid, wherein said epoxidized fatty acid alkyl esters comprise epoxidized fatty acid methyl esters.

7. The process of claim 1, wherein said removing of step (b) does not comprise azeotropic distillation, wherein said removing of step (b) does not comprise washing said epoxidized reaction mixture with water.

8. A plasticizer comprising at least a portion of said fatty acid alkyl esters of claim 1.

9. A polymeric composition comprising a polymeric resin and at least a portion of said fatty acid alkyl esters of claim 1.

10. The composition of claim 9, wherein said polymeric resin is polyvinyl chloride.

11. The process of claim 2, wherein said removing of step (b) comprises subjecting said epoxidized reaction mixture to layer separation, thereby forming an organic phase and an aqueous phase, and further comprising subjecting at least a portion of said organic phase to vacuum distillation, thereby forming said intermediate reaction mixture.

12. The process of claim 2, wherein said intermediate reaction mixture has an acid value of less than 1 mg KOH/g.

13. The process of claim 2, wherein said epoxidized fatty acid alkyl esters have an APHA color value of less than 100.

14. The process of claim 2, wherein said peroxide comprises hydrogen peroxide, wherein said acid comprises formic acid, wherein said epoxidized fatty acid alkyl esters comprise epoxidized fatty acid methyl esters.

15. The process of claim 2, wherein said removing of step (b) does not comprise azeotropic distillation, wherein said removing of step (b) does not comprise washing said epoxidized reaction mixture with water.

16. A plasticizer comprising at least a portion of said fatty acid alkyl esters of claim 2.

17. A polymeric composition comprising a polymeric resin and at least a portion of said fatty acid alkyl esters of claim 2.

18. The composition of claim 17, wherein said polymeric resin is polyvinyl chloride.

* * * * *